United States Patent [19]

Mezack et al.

[11] Patent Number: 5,645,068
[45] Date of Patent: Jul. 8, 1997

[54] METHODS AND APPARATUS FOR AMBULATORY AND NON-AMBULATORY MONITORING OF PHYSIOLOGICAL DATA USING DIGITAL FLASH STORAGE

[75] Inventors: Gary P. Mezack, Norco, Calif.; James H. Luby, Oklahoma City, Okla.

[73] Assignee: BioScan, Inc., Oklahoma City, Okla.

[21] Appl. No.: 407,303

[22] Filed: Mar. 20, 1995

[51] Int. Cl.$^6$ .................................................. A61B 5/0205
[52] U.S. Cl. ........................................ 128/670; 128/700
[58] Field of Search ................................ 128/670, 700, 128/702, 731, 733, 716; 364/413.06, 413.02, 413.03

[56] References Cited

U.S. PATENT DOCUMENTS

| | | |
|---|---|---|
| Re. 29,921 | 2/1979 | Cherry et al. . |
| D. 310,120 | 8/1990 | Wickham et al. . |
| 3,215,136 | 11/1965 | Holter et al. . |
| 4,346,718 | 8/1982 | Morris . |
| 4,364,397 | 12/1982 | Citron et al. . |
| 4,367,753 | 1/1983 | Jirak . |
| 4,417,306 | 11/1983 | Citron et al. . |
| 4,493,327 | 1/1985 | Bergelson et al. . |
| 4,519,398 | 5/1985 | Lisiecki et al. . |
| 4,528,988 | 7/1985 | Wong . |
| 4,531,527 | 7/1985 | Reinhold, Jr. et al. . |
| 4,532,934 | 8/1985 | Kelen . |
| 4,546,436 | 10/1985 | Schneider et al. . |
| 4,583,553 | 4/1986 | Shah et al. . |
| 4,592,018 | 5/1986 | Wiegman . |
| 4,678,144 | 7/1987 | Cox et al. . |
| 4,883,065 | 11/1989 | Kelen . |
| 4,920,489 | 4/1990 | Hubelbank et al. . |
| 5,016,009 | 5/1991 | Whiting et al. ............ 364/715.02 |
| 5,027,824 | 7/1991 | Dougherty et al. . |
| 5,090,418 | 2/1992 | Squires et al. . |
| 5,092,341 | 3/1992 | Kelen . |
| 5,109,862 | 5/1992 | Kelen et al. . |
| 5,187,657 | 2/1993 | Forbes . |
| 5,205,295 | 4/1993 | Del Mar et al. . |
| 5,228,450 | 7/1993 | Sellers . |
| 5,238,001 | 8/1993 | Gallant et al. ............... 128/700 |
| 5,305,202 | 4/1994 | Gallant et al. . |
| 5,305,761 | 4/1994 | Byrne et al. . |
| 5,343,870 | 9/1994 | Gallant et al. . |
| 5,355,891 | 10/1994 | Wateridge et al. . |

*Primary Examiner*—William E. Kamm
*Assistant Examiner*—Kennedy J. Schaetzle
*Attorney, Agent, or Firm*—Jones, Day, Reavis & Pogue

[57] ABSTRACT

A battery operable ambulatory and non-ambulatory patient monitoring system that includes storage to a solid-state flash memory which storage is controlled in a manner to optimize power consumption, to have a variable sampling rate, to have up to 24 input data channels and to provide as an option loss-less data compression in the processor.

17 Claims, 6 Drawing Sheets

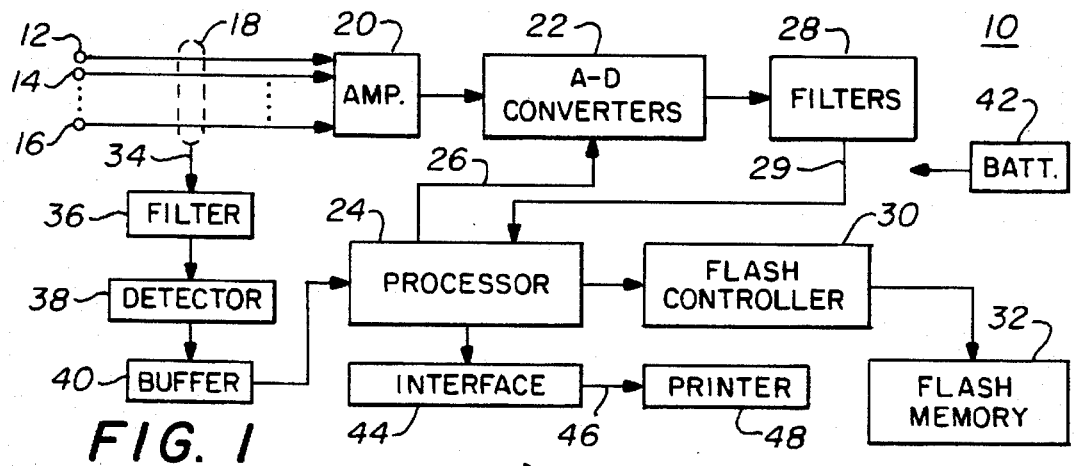
FIG. 1
INFF= INPUT PIN LATCHES
OPAD= INPUT OR OUTPUT PAD
IPAD= INPUT PAD
M3-1= 3 to 1 MULTIPLEXER
M4-2= 4 to 2 MULTIPLEXER
OBUF= OUTPUT BUFFER TO PAD
IBUF= INPUT BUFFER FROM PAD
OBUFZ= TRI-STATE OUTPUT BUFFER
RD8= 8 BIT D TYPE LATCH
D3-8= 3 BIT TO 8 LINE DECODER
C16BARD= 4 BIT COUNTER
FIG. 2
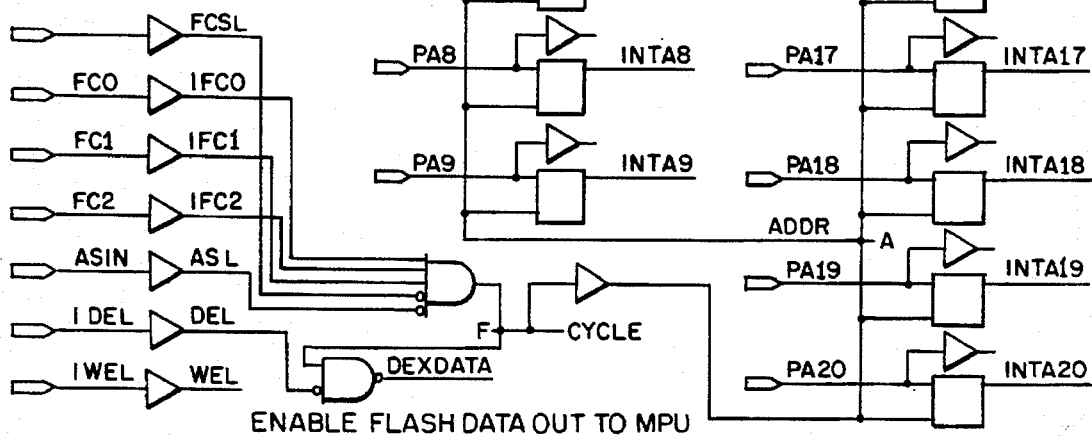

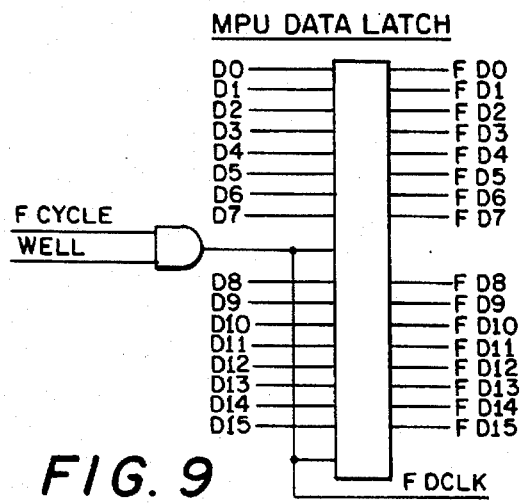
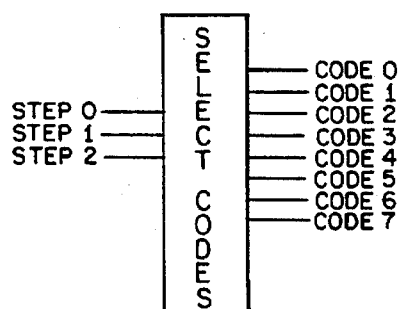
FIG. 9
FIG. 10
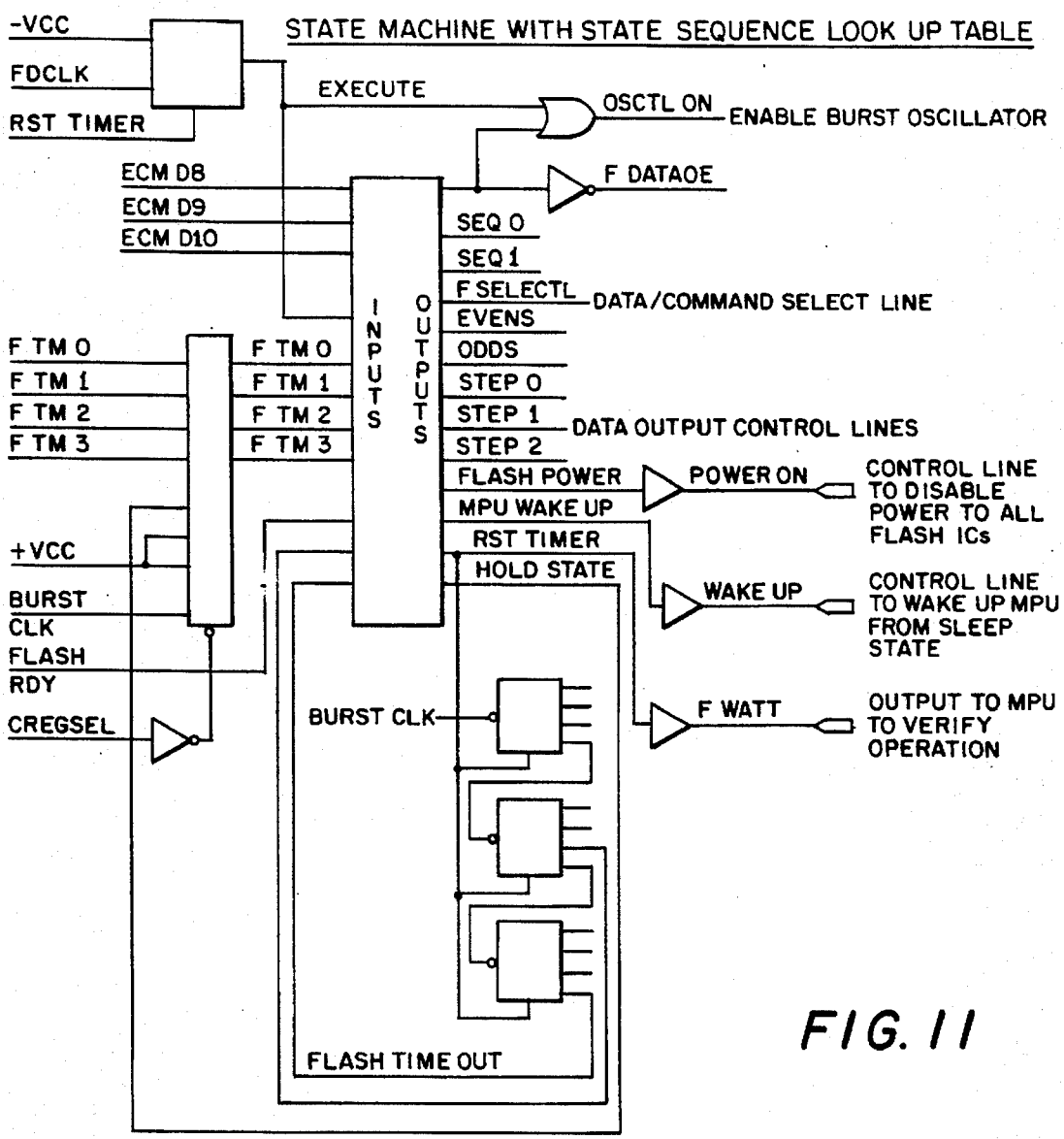
FIG. 11

SECTOR ERASE SEQUENCE

|  | ADDRESS | DATA |
|---|---|---|
| STEP 1 | 5555 | AA |
| STEP 2 | 2AAA | 55 |
| STEP 3 | 5555 | 80 |
| STEP 4 | 5555 | AA |
| STEP 5 | 2AAA | 55 |
| STEP 6 | 5 BIT SECTOR ADDR. | 30 |
| STEP 7 | WAIT FOR READY | |

FIG. 12a

BYTE WRITE SEQUENCE

|  | ADDRESS | DATA |
|---|---|---|
| STEP 1 | 5555 | AA |
| STEP 2 | 2AAA | 55 |
| STEP 3 | 5555 | A0 |
| STEP 4 | DATAs ADDR. | NEW DATA |
| STEP 5 | WAIT FOR READY | |

ADDR. FROM MPU ADDR. REGISTER
DATA FROM MPU DATA REGISTER

FIG. 12b

CHIP ERASE SEQUENCE

|  | ADDRESS | DATA |
|---|---|---|
| STEP 1 | 5555 | AA |
| STEP 2 | 2AAA | 55 |
| STEP 3 | 5555 | 80 |
| STEP 4 | 5555 | AA |
| STEP 5 | 2AAA | 55 |
| STEP 6 | 5555 | 10 |
| STEP 7 | WAIT FOR READY | |

TYP = 16 sec

FIG. 12c

RESET/READ SEQUENCE

|  | ADDRESS | DATA |
|---|---|---|
| STEP 1 | 5555 | AA |
| STEP 2 | 2AAA | 55 |
| STEP 3 | 5555 | F0 |
| STEP 4 | DATAs ADDR. | NEW DATA |

ADDR. FROM MPU ADDR. REGISTER
NEW DATA FROM FLASH LOCATION

FIG. 12d

METHODS AND APPARATUS FOR AMBULATORY AND NON-AMBULATORY MONITORING OF PHYSIOLOGICAL DATA USING DIGITAL FLASH STORAGE

BACKGROUND OF THE INVENTION

1. Field of the Invention

This invention relates generally to battery operable ambulatory and non-ambulatory patient monitoring systems and in particular to an ambulatory patient monitoring device that includes storage to a solid-state flash memory which storage is controlled in a manner to optimize power consumption.

2. Description of Related Art

Ambulatory monitoring of patient data is well known in the art and is useful in monitoring the health of the patient. There are many types of patient physiological parameters that need to be monitored for particular medical examinations. The most prominent type of ambulatory monitoring is ECG monitoring. Such ambulatory ECG monitoring systems are also known as Holter monitors. The ECG data is acquired by the Holter monitor continuously over a fixed period, generally twenty-four hours. Such devices are described in U.S. Pat. Nos. 5,228,450; 5,205,295; and 5,027,824, each of which is incorporated herein by reference in its entirety.

While the Holter monitor is a well-known ambulatory device for ECG measurements, other ambulatory devices have been developed for monitoring brain wave functions and are known as ambulatory EEG devices. U.S. Pat. No. 5,222,503 discloses a history of such devices and is incorporated herein by reference in its entirety.

It has also been discovered that in the field of sleep disorders, a correct diagnosis should include details of the ECG, the EEG, the EMG (muscle measurement), EOG (rapid eye movement or REM), respiratory activities such as breathing or airflow, respiratory physical response such as movement of the chest or stomach, and blood oxygen saturation. To be effective, all of these different physiological parameters must be analyzed simultaneously. In the analysis of various physiological conditions, it may be extremely important to correlate the ECG, the EEG, the EMG, the EOG, the respiratory activity, the respiratory mechanics, and blood oxygen saturation. At present, it is impossible to provide such correlation using a portable battery operable device. A sleep monitoring device is disclosed in U.S. Pat. No. 5,187,657, incorporated herein by reference in its entirety.

Conventional ambulatory ECG Holter monitors have fallen into two categories: cassette tape-based systems and solid-state systems. They are worn by the patient outside the hospital during the patient's normal daily routine. Tape based systems comprise a magnetic tape recorder that records ECG signals on to the cassette tape from electrodes that are attached to the patient in a predefined fashion. On completion, the tape is removed from the recorder and the ECG data stored on the cassette tape are analyzed usually on a personal computer-based scanning system.

There are numerous problems with the tape-based systems. Primarily, the cassette tapes have a limited frequency response. The maximum frequency response of such tapes is around 40 Hz. But, conventional diagnostic ECG systems require a frequency range from 0.1 Hz to 100 Hz. Further, the latest high resolution EGG analysis require that data should be recorded to at least 300 Hz. Moreover, for high resolution ECG devices, the devices should have the capability to record a minimum of 1000 samples per second. Such high fidelity recording is not possible on tape-based systems. The highest frequency response of the magnetic tape devices is further limited by the small recording range on the tape. In addition, tape-based systems suffer from motion error problems including speed changes and recording head tracking errors. These problems are further compounded by the recorder's inability to precisely encode important events such as abnormal heart beats and pacemaker spikes on the tapes.

Solid-state systems consist of solid-state memory that digitally stores the ECG data. ECG data are recorded and stored to this memory for future analysis. In solid-state systems, in order to store the enormous amounts of data, the prior art units have relied on severe data compression, with a resultant distortion of the data. Typically, such devices have a memory capacity of 2-to-4 megabytes when, in fact, they should have in the neighborhood of 30-to-80 megabytes. Because the data must be compressed enormously for memory capacity, serious loss of data occurs. In U.S. Pat. No. 5,222,503, the memory device is a separate unit worn about the waist of the patient. Also, because of the amount of data that must be stored, power requirements for the units are significantly increased. Further, they use typically volatile memories so that the data held in the memory is lost upon an interruption of power which is not uncommon in battery operated devices. Recently, an ambulatory ECG monitor was introduced which incorporated a miniature hard disk drive for data storage. This electromechanical design is covered by U.S. Pat. No. 5,228,450. Systems that employ non-volatile memory in the form of miniature hard disk drives for mass data storage have moving parts that may damage the data in harsh environments typical to Holter monitoring. Further, systems that use non-volatile memory units such as PCMCIA memory cards do not have the cards built into the monitor. Instead, they are attached to the monitor through a connector. In such systems, the memory card may get disconnected in the middle of a recording. Furthermore, such cards, unlike cassette tapes, are very expensive and might be easily lost or misplaced.

A recent article in *The American Journal of Cardiology*, Vol. 68, Oct. 15, 1991, entitled "Combined Ambulatory Electroencephalographic and Electrocardiographic Recordings for Evaluation of Syncope", presented good clinical results for a subset of the syncope (fainting or lightheadedness) population. In the study, both an ambulatory 2 channel ECG recording system and an ambulatory EEG recording system (including 7 channels of EEG and 1 channel of ECG) were connected to the patients for 24 hours with two separate ambulatory monitors, one for ECG and one for EEG. The present innovative design would allow this clinical information (i.e., both cardiology and neurology workups) with one study because only one ambulatory monitor would be used.

It would be advantageous to provide an ambulatory or portable device for storing patient physiological data to be used for subsequent medical diagnosis in which the device could monitor a plurality of channels having data representing patient physiological data such as ECG, EEG, EMG, EOG, respiratory activities, respiratory mechanics, and blood oxygen saturation simultaneously or in such combinations as needed.

Further, it would be advantageous to have such an ambulatory monitoring device in which a plurality of input channels have analog physiological data thereon and in which one or more channels of one or more of said physiological parameters such as 2 or 3 channels of ECG and 7 channels of EEG for a syncope study could be selectively accessed for recording.

Further, it would also be advantageous to have such an ambulatory monitoring device in which a plurality of input channels having analog physiological data can be converted to digital samples on each separate one of the channels selected at an individually selectable sampling rate for converting the raw analog data in each channel to raw digital data for recording.

It would also be advantageous to have a battery-operated ambulatory monitoring device which had a high capacity flash memory for storing large amounts of data but which could be controlled by a flash memory controller applied specifically to storing both raw data and appropriate measurement data in the flash memory with optimum power usage.

It would be further advantageous to have such an ambulatory monitoring device that employs flash memory built into the device for mass storage of a plurality of input signals that does not suffer from the power consumption and other problems of tape-based systems, solid-state systems, and other systems using the hard disk drives and PCMCIA memory cards.

SUMMARY OF THE INVENTION

The present invention relates to an ambulatory or portable monitoring device that has a plurality of input channels for receiving raw analog data signals from patient sensors representing patient physiological data such as ECG, EEG, EMG, EOG, respiratory activities, respiratory mechanics, and blood oxygen saturation. The invention includes a set of electrodes or other means such as transducers for obtaining such physiological data. The invention also includes A-to-D converters to convert these analog data signals into digital data signals. The analog physiological data on each separate one of the channels can be sampled at an individually selectable rate for converting the raw analog data in each channel to raw digital data. The invention further utilizes a processor to take appropriate measurements of the raw digital data. Further, a non-volatile flash memory is utilized to store both the raw data and the appropriate measurement data with the use of a flash memory controller. The flash memory controller is applied specifically to the storage of the raw data and the appropriate measurement data with optimum power usage. In addition, the processor selects one or more channels of one or more of the physiological parameters for recording. This enables various combinations of the input signals to be recorded for analysis of a particular physiological condition. For instance, with the monitoring of ECG, three ECG sensor electrodes can be selected by the computer and monitored as is the typical case. Further, if the physician so desires, he can select not only the monitoring of the three ECG channels but also as many EEG channels as desired so that correlation of brain wave activity and heart activity can be accomplished by the physician. Obviously, other combinations of the sensor selection could be utilized such as, during analysis of sleep apnea, monitoring of all of the channels set forth above for correlation simultaneously at a given event.

Thus, it is an object of the present invention to provide a battery-operated ambulatory or portable monitor that includes a plurality of sensors for attachment to an ambulatory patient for providing analog signals representing different physiological parameters.

It is also an object of the present invention to provide an ambulatory monitor in which one or more channels of one or more physiological parameters can be selectively recorded.

It is still another object of the present invention to provide an ambulatory monitoring device in which analog physiological data on a plurality of selected input channels can be converted to digital samples on each separate one of the selected channels selected at an individually selectable sampling rate for converting the raw analog data in each channel to raw digital data.

It is yet another object of the present invention to provide a battery-operated ambulatory monitoring device that comprises a mass memory storage that is a flash memory having the capacity to store data in the range of 50-to-500 megabytes.

It is also another object of the present invention to provide a flash memory controller applied specifically to storing both raw data and appropriate measurement data in the flash memory with optimum power usage, so that measurement data can be correlated with the raw data.

It is another object of the present invention to have a solid-state ambulatory monitoring device that utilizes flash memory built into the device and that does not suffer from possible data loss caused by the failure of moving parts as in monitors based on cassette tapes or hard disk drives.

It is yet another object of the present invention to have a solid-state ambulatory monitoring device that utilizes flash memory built into the monitor that does suffer from loss or misplacement of the recorded physiological data as is possible in PCMCIA memory card-based monitors.

It is also an object of the present invention to have a solid-state battery operated portable monitoring device with a plurality of sensors that can be attached to a non-ambulatory patient so as to record one or more physiological parameters in a typical non-ambulatory setting such as a sleep study.

Thus, the present invention relates to a monitoring device for recording physiological data to be used for subsequent medical diagnosis and comprising a plurality of input channels for receiving raw analog data signals representing the patient physiological data such as ECG, EEG, EMG, EOG, respiratory activities, respiratory mechanics, and blood oxygen saturation. An analog-to-digital converter samples the analog physiological data on each separate one of the channels at an individually selectable rate for converting the raw analog data samples in each channel to raw digital data. A digital signal processor receives the raw digital data from the analog-to-digital converter and takes appropriate measurements of the raw digital data for storage. A non-volatile flash memory is coupled to the processor for storing both the raw data and the appropriate measurement data. A flash memory controller is coupled between the processor and the flash memory to enable storage of the raw data and appropriate measurement data in the memory with optimum power usage.

The invention also relates to a method for recording and storing physiological patient data to be used for subsequent medical diagnosis in an ambulatory or portable monitoring device. The method comprises the steps for receiving raw analog data signals representing patient physiological data on a plurality of input channels where the input channels include data such as ECG, EEG, EMG, EOG, respiratory activities, respiratory mechanics, and blood oxygen saturation, sampling the analog physiological data on each separate one of the channels at an individually selectable rate with analog-to-digital converters for converting the raw analog data samples in each channel to raw digital data, taking appropriate measurements of the raw digital data with a processor, coupling a non-volatile flash memory to the processor for storing both the raw data and the appropriate measurement data, and coupling a flash memory controller between the processor and the flash memory to enable storage of the raw data and appropriate measurement date in the memory with optimum power usage.

BRIEF DESCRIPTION OF THE DRAWINGS

These and other features of the present invention will be more fully disclosed when taken in conjunction with the following DETAILED DESCRIPTION OF THE DRAWINGS in which like numerals represent like elements and in which:

FIG. 1 is a block diagram setting forth the apparatus of the present invention; and FIGS. 2–12 are circuit diagrams of components forming the flash memory controller.

DETAILED DESCRIPTION OF THE DRAWINGS

Figure 3:
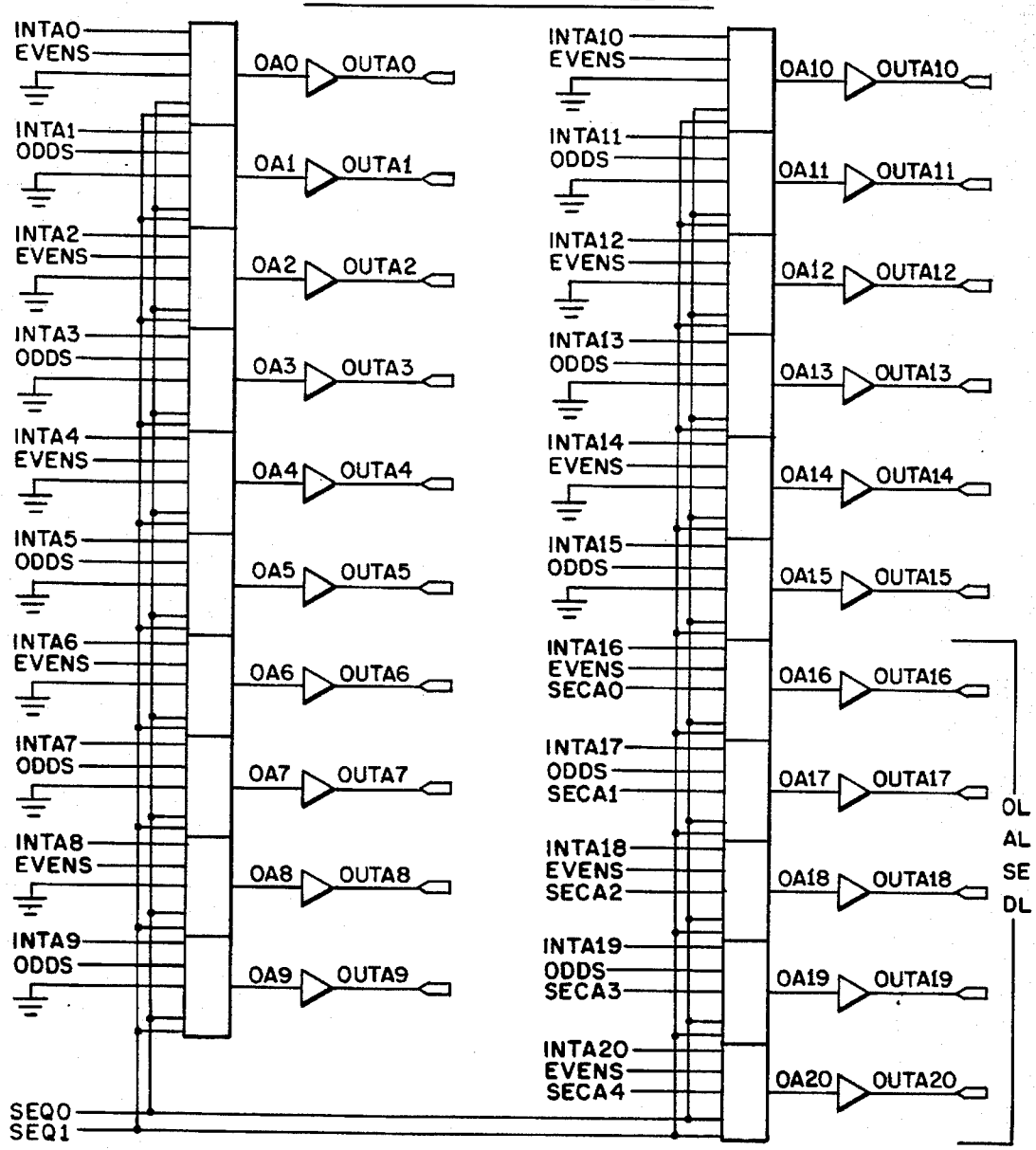

The ambulatory monitoring device 10 of the present invention is shown in FIG. 1. It includes n sensors 12, 14, and 16 that can be attached to the body of a patient and where n is in the range of 1 to at least 24 input sensors. The sensors 12, 14, and 16 are coupled via input connectors or channels 18 to n amplifiers 20, one for each of the n channels.

A like number of analog-to-digital converters 22 are provided for the n channels with the particular channels for sensors 12, 14, and 16 being selected by the digital signal processor 24 through one of a plurality of connectors 26. Thus, if the physician desires to utilize three ECG channels and one EEG channel, or three ECG channels and seven EEG channels, the processor 24 will couple the appropriate analog-to-digital converters 22 to the appropriate input channels 1–24. The sampling rate of the analog-to-digital converters 22, which are well known in the art, is variable in a well-known manner at a rate from 50-to-2000 samples per second. Again, the sampling rate can be selected by the physician through the digital signal processor 24 generating the appropriate signal on one of connectors 26 in a well-known manner. After the analog-to-digital converters 22 have sampled the analog physiological data on each separate one of the selected channels at the individually selected sampling rate to convert the raw analog data samples in each channel to raw digital data, the data is coupled to the data filter and buffer ASIC 28. The filters 28 have a bandwidth from 0.05-to-1000 Hz, thus capturing all of the raw data being coupled to the digital signal processor 24 on line 29.

The digital signal processor 24 takes appropriate measurements of the raw digital data. These appropriate measurements may include QRS signal measurements for cardiac analysis, the presence or absence of a heart beat, the heart-beat rate, an arrhythmic event, R-wave occurrences, ST segment analysis, tachycardia, brain waves and the like.

The output of the processor 24 is coupled directly to a flash ASIC memory controller 30, a device normally well known in the art, but which has been uniquely modified as described hereafter to control the storage of data in a flash memory 32 in such a manner as to conserve battery power. The flash ASIC controller 30 controls the data storage from the digital signal processor 24 to the flash memory 32.

If desired, the processor 24 can use a known technique for providing loss-less compression of the data which, again, is stored in flash memory 32 under the control of the flash controller 30 as explained hereafter and as described in U.S. Pat. No. 5,016,009.

Also, if desired, heart pacemaker data can be processed on channels 34 through filters 36, detectors 38, and additional filters and buffers 40 where the data is then fed to the digital signal processor 24. Again, this pacemaker data can be stored in the flash memory 32 under the direction of flash controller 30. Batteries 42 provide power for all of the units shown in the figure. When desired for analysis, the data stored in the flash memory can be coupled to processor 24 and through high speed interface 44 and a cable 46 directly to a printer board 48 for coupling to an analyzer. Thus the processor 24 can connect, via interface block 44, directly to printer 48 to dump its data.

The flash controller 30 is a modified version of one well known in the art. A typical flash memory device that this controller could control is an AM29f016 by AMD. This controller is modified and specialized to perform the following unique functions to provide extremely low power operation:

(1) It buffers the data from the microprocessor 24 in blocks for later write operations.

(2) It prepares the flash memory 32 array for storing blocks of data.

(3) It controls the power to the flash memory 32 so that it is powered down between block writing operations. Since data from the processor 24 is stored in blocks, the processor 24 then is allowed to "sleep" or is powered down between data transfers so that it is not consuming power during the block writing operation. Therefore, the flash controller 30 sends the necessary signals to the processor 24 to cause power to be applied to it, or to "wake it up" from a sleep state. This is done when the flash memory 32 has the last data block stored therein and is ready for another.

(4) The flash controller 30 allows for simultaneous operations in one or more flash memory chips 32.

FIGS. 2–12 disclose the components in the modified flash memory controller.

FIG. 2 is the input address register circuit receiving data from the MPU.

FIG. 3 is the flash address multiplexer circuit.

Figure 4:
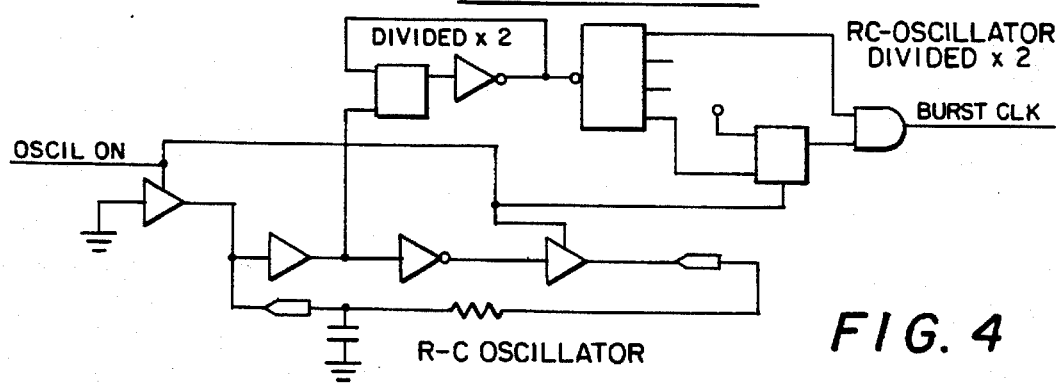

FIG. 4 is the burst oscillator circuit.

Figure 5:
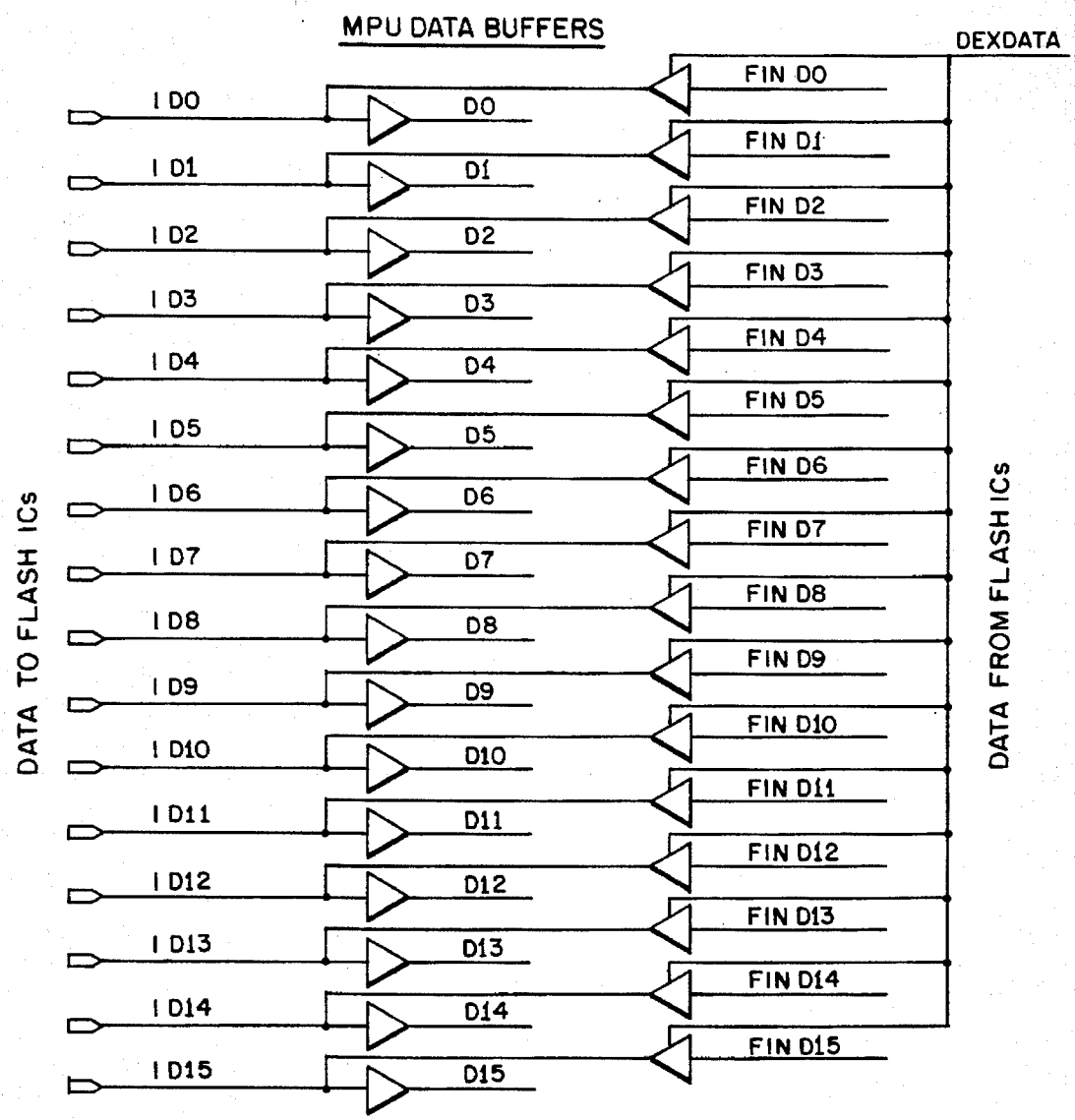

FIG. 5 discloses the MPU data buffers.

Figure 6:
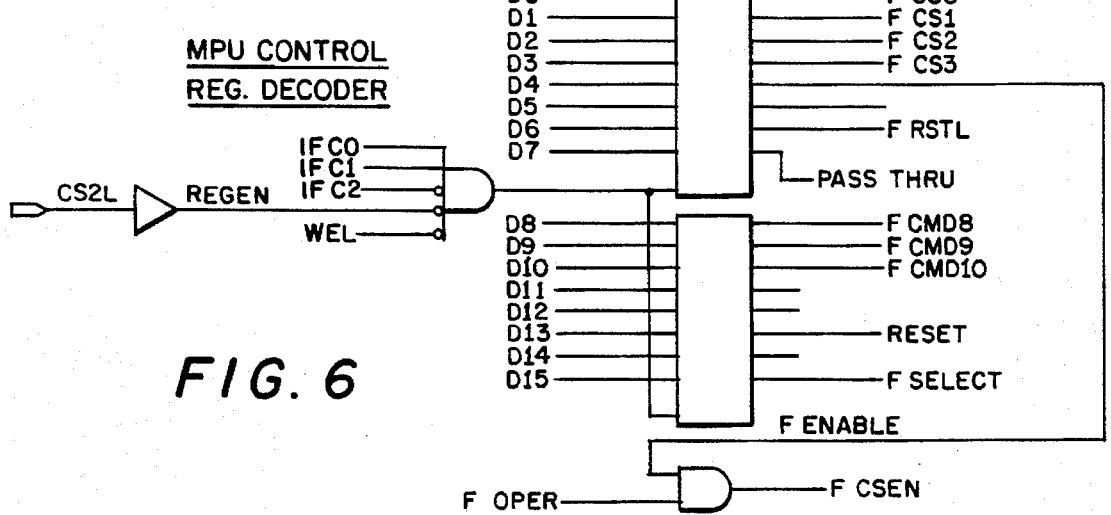

FIG. 6 is the MPU control register circuit.

Figure 7:
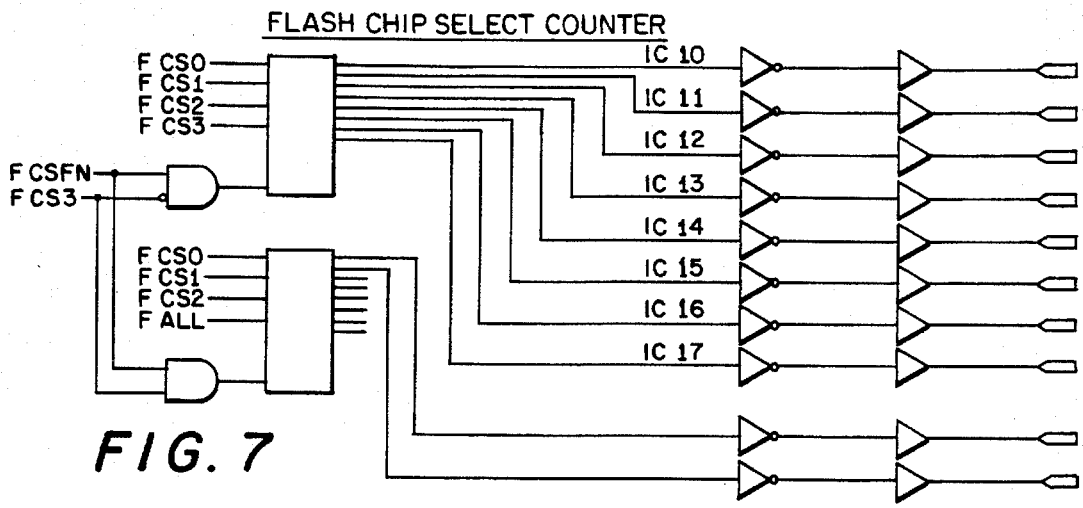

FIG. 7 is the flash chip selector circuit.

Figure 8:
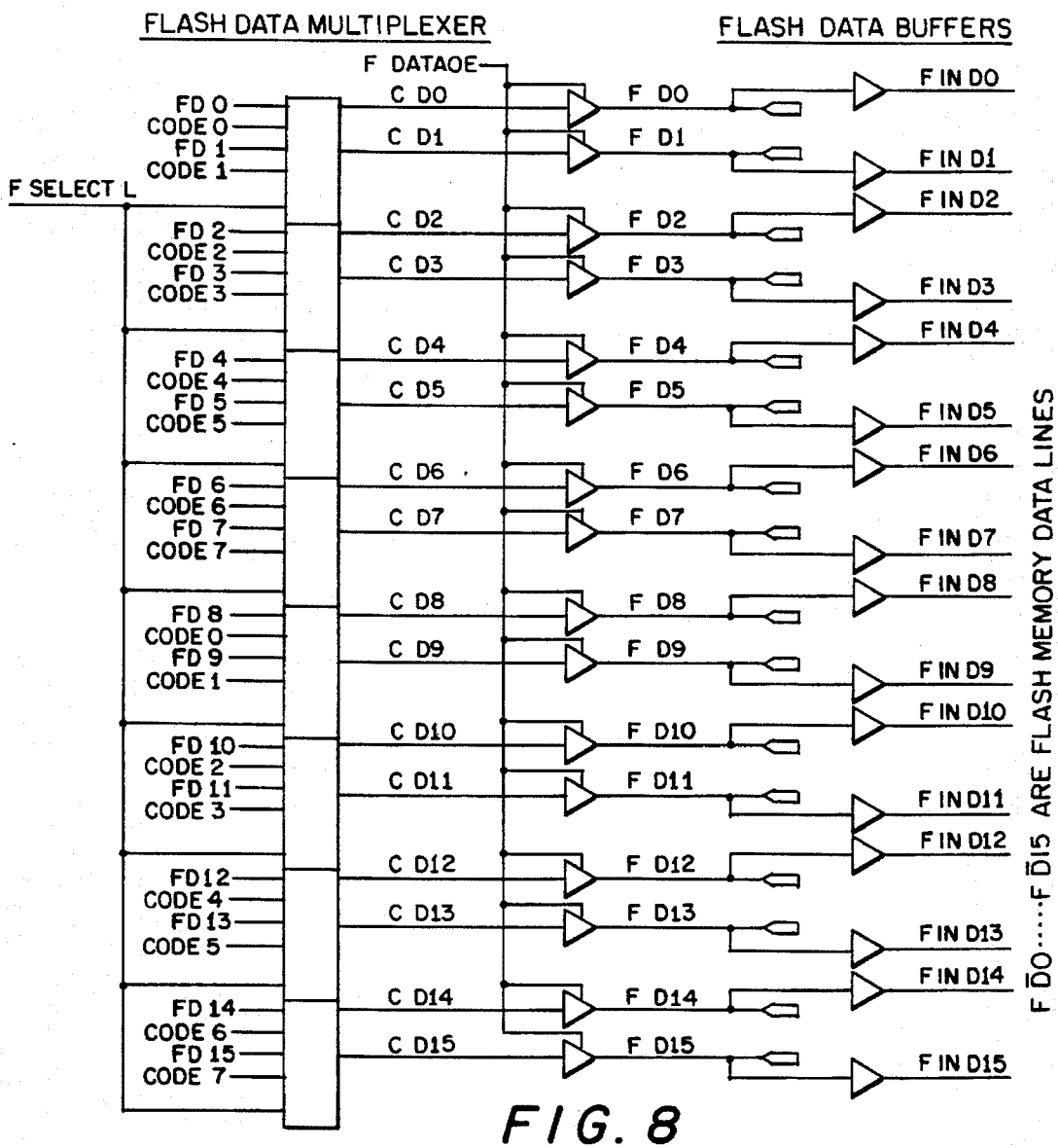

FIG. 8 is the flash data multiplexer circuit and the flash data buffers.

FIG. 9 is the MPU data latch circuit.

FIG. 10 is the data command look-up table circuit.

FIG. 11 is the state machine with sequence look-up table and time-out counters.

FIG. 12 is a table showing the AMD29f016 flash memory control sequences.

Upon power-up the controller 30 is inactive and the flash memory array 32 is reset and power is applied. The MPU 24 may read from the lowest flash memory 32 IC chips. The controller 30 has five modes of operation. These modes are: (0) read 16 bits of data, (1) erase entire chip(s), (2) erase sectors, (3) reset chip(s), and (4) write 16 bits of data. The command sequences are listed in a table presentation in FIG. 12.

To operate Mode 0 and read 16 bits of data from the flash memory 32, the MPU 24 follows the following sequence:

1. Write the chip select code and the appropriate command code into the MPU control register shown in FIG. 6.

2. Read from the flash controller 30 in a normal MPU 24 operation. The flash controller 30 will statically generate the appropriate chip selects and direct the flash data to the MPU 24.

To operate Mode 1 and erase the entire chip(s) of flash memory 32, the MPU 24 uses the following sequence:

1. The MPU 24 presets the wake-up routine for execution when the erase is completed or times-out.
2. The MPU 24 writes the chip select code and the appropriate command code into the MPU control register shown in FIG. 6, and the address of the block to erase, into the MPU 24 input address register shown in FIG. 2. The MPU 24 may power down and await "wake up" via the flash memory controller 30.
3. The flash controller 30 is activated by writing to the input address register in FIG. 2 and initiating the following sequence:
   A. Start the burst oscillator in FIG. 4 and the state machine shown in FIG. 11.
   B. Then, sequence the address of 5555h from the data command look-up table shown in FIG. 12(c) with data of AAh onto the flash chip lines via the multiplexer shown in FIG. 3 and the data latch in FIG. 9. Pulse one or all of the chip select lines and other chip control lines via the flash chip select control circuit in FIG. 7 in order to write this first unlock step. The single or multiple chip select(s) is determined by the command stored in the MPU 24 command register.
   C. Next, sequence the address of 2AAAh in FIG. 12(c) with data of 55h onto the flash chip lines. Pulse one or all of the chip select lines and other chip control lines via the control circuit in FIG. 7 to write this second unlock step.
   D. In the next step, sequence the address of 5555h in FIG. 12(c) with data of 80h onto the flash chip lines. Pulse one or all of the chip select lines and other chip control lines via the control circuit in FIG. 7 to write this third unlock step and send the command to the flash chips.
   E. Then, sequence the address of 5555h in FIG. 12(c) with data of AAh onto the flash chip lines. Pulse one or all of the chip select lines and other chip control lines via the control circuit in FIG. 7 to write this fourth unlock step.
   F. Next, sequence the address of 2AAAh in FIG. 12(c) with data of 55h onto the flash chip lines. Pulse one or all of the chip select lines and other chip control lines via the control circuit in FIG. 7 to write this fifth unlock step.
   G. Finally, sequence the address of 5555h in FIG. 12(c) with data of 10h onto the flash chip lines. Pulse one or all of the chip select lines and other chip control lines via the control circuit in FIG. 7 to write this sixth command to the flash chips.
   H. Wait for the Ready line from the flash or a maximum time-out measured by the circuit of FIG. 11.
4. The MPU 24 is sent a wake-up command when the state machine shown in FIG. 11 completes the sequence and then the MPU 24 executes the previously setup routine.

To operate Mode 2 and erase a sector of flash memory 32, the MPU 24 follows the following sequence shown in FIG. 12(a):

1. The MPU 24 presets the wake-up routine to execute when the erase is completed or times-out.
2. Write the chip select code and the appropriate command code into the MPU control register shown in FIG. 6 and the address of the block to erase into the MPU input address register shown in FIG. 2. The MPU 24 may power down and await "wake up" via the flash memory controller 30.
3. The flash controller 30 is activated by the writing of data in the address register shown in FIG. 2 and initiates the following sequence:
   A. Start the burst oscillator shown in FIG. 4 and the state machine shown in FIG. 11.
   B. Sequence the address of 5555h shown in FIG. 12(a) with data of AAh onto the flash chip lines via the flash address multiplexer shown in FIG. 3 and the flash data multiplexer shown in FIG. 8. Pulse one or all of the chip select lines and other chip control lines via the control circuit shown in FIG. 7 in order to write this first unlock step. The single or multiple chip select(s) is determined by the command stored in the MPU 24 command register.
   C. Sequence the address of 2AAAh shown in FIG. 12(a) with data of 55h onto the flash chip lines. Pulse one or all of the chip select lines and other chip control lines to write this second unlock step.
   D. Sequence the address of 5555h shown in FIG. 12(a) with data of 80h onto the flash chip lines. Pulse one or all of the chip select lines and other chip control lines to write this third unlock step and send the command to the flash chips in memory 32.
   E. Sequence the address of 5555h with data of AAh onto the flash chip lines. Pulse one or all of the chip select lines and other chip control lines to write this fourth unlock step.
   F. Sequence the address of 2AAAh with data of 55h onto the flash chip lines. Pulse one or all of the chip select lines and other chip control lines to write this fifth unlock step.
   G. Sequence the address of the sector to be erased with data of 30h onto the flash chip lines. Pulse one or all of the chip select lines and other chip control lines to write this final command.
   H Wait for the Ready line from the flash memory or a maximum time-out measured by the circuit of FIG. 11.
4. The MPU 24 is sent a wake-up command when the state machine shown in FIG. 11 completes the sequence and then the MPU 24 executes the previously set-up routine.

To operate Mode 3 and reset a chip of the flash memory 32, the MPU follows the following sequence:

1. The MPU 24 presets the wake-up routine to execute when the reset is completed or times-out.
2. The chip select code and the appropriate command code are written into the MPU control register shown in FIG. 6 and the address of the chip to reset into the MPU input address register shown in FIG. 2. The MPU 24 may power down and await "wake up" via the flash memory controller 30.
3. The flash controller 30 is activated by the writing of the address in the input register shown in FIG. 2 and initiates the following sequence:
   A. Start the burst oscillator shown in FIG. 4 and the state machine shown in FIG. 11.
   B. Sequence the address of 5555h shown in FIG. 12(d) with data of AAh onto the flash chip lines via the flash address multiplexer shown in FIG. 3 and the select control shown in FIG. 7. Pulse one of the chip select lines and other chip control lines via select control shown in FIG. 7 in order to write this first unlock step.

C. Sequence the address of 2AAAh with data of 55h onto the flash chip lines. Pulse one of the chip select lines and other chip control lines to write this second unlock step.

D. Sequence the address of 5555h with data of 80h onto the flash chip lines as shown in step 3 of FIG. 12(c). Pulse one of the chip select lines and other chip control lines to write this third unlock step and send the command to the flash chips.

E. Sequence the address of 5555h with data of F0h onto the flash chip lines as shown in step 3 if FIG. 12(d). Pulse one of the chip select lines and other chip control lines to write this fourth unlock step.

F. Sequence the address from the input address register shown in FIG. 2 onto the address lines and read the status of the flash chip from the data lines directed to the MPU via MPU data buffers shown in FIG. 5 and the flash data buffers shown in FIG. 8

G. Wait for the Ready line from the flash or a maximum time-out measured by the circuit in FIG. 11.

4. The MPU 24 is sent a wake-up command when the state machine shown in FIG. 11 completes the sequence and then the MPU 24 executes the previously set-up routine.

To operate in Mode 4 and write 16 bits of data into the flash memory 32, the MPU24 follows the following sequence:

1. The MPU24 presets the wake-up routine to execute when the data write is completed or times-out.

2. Write the chip select code and the appropriate command code into the MPU control register shown in FIG. 6. The MPU 24 must also write the address of the word to write into the MPU input address register shown in FIG. 2 along with the 16 bit data to be written into the flash memory 32. The MPU 24 may power down and await "wake up" via the flash memory controller 30.

3. The flash controller 30 is activated by the writing to the address register shown in FIG. 2 and initiates the following sequence as shown in FIG. 12(b).

A. Start the burst oscillator shown in FIG. 4 and the state machine shown in FIG. 11.

B. Sequence the address of 5555h with data of AAh onto the flash chip lines via the flash address multiplexer shown in FIG. 3 and the flash data multiplexer shown in FIG. 8. Pulse one or all of the chip select lines and other chip control lines via the flash chip select control shown in FIG. 7 in order to write this first unlock step. The single or multiple chip select(s) is determined by the command in the MPU command register.

C. Sequence the address of 2AAAh with data of 55h onto the flash chip lines. Pulse one or all of the chip select lines and other chip control lines to write this second unlock step.

D. Sequence the address of 5555h with data of A0h onto the flash chip lines. Pulse one or all of the chip select lines and other chip control lines to write this third unlock step and send the command to the flash chips.

E. Sequence the address of the byte to be written along with the data to be written onto the flash chip lines via the flash address multiplexer shown in FIG. 3 and the flash data multiplexer shown in FIG. 8. Pulse one or all of the chip select lines and other chip control lines to start the write operation in the flash IC via the flash chip select control circuit shown in FIG. 7.

H. Wait for the Ready line from the flash or a maximum time-out measured by the circuit shown in FIG. 11.

4. The MPU 24 is sent a wake-up command when the state machine shown in FIG. 11 completes the sequence and then the MPU executes the previously set-up routine.

Thus, the flash ASIC controller 30 minimizes power usage by operating in a burst mode for all storage operations, thereby eliminating the need for continuous high-speed clocking. Because the interface between the processor or CPU 24 and the flash ASIC controller 30 is a software interface, it is device independent insofar as the processor 24 is concerned.

Thus, there has been disclosed a novel ambulatory monitoring device for recording patient physiological data to be used for subsequent medical diagnosis. The device can monitor up to 24 channels of data selectively. The data selected may be any combination of ECG data, EEG data, EMG data, EOG data, respiratory activity data, respiratory mechanics data:, and blood oxygen saturation data. The novel invention samples the analog physiological data on each separate one of the channels at an individually selectable rate and converts the raw analog data samples in each channel to raw digital data. A processor receives the raw digital data and takes appropriate measurements of the raw digital data for storage. The appropriate measurements will, of course, relate to the type of medical analysis being performed. A non-volatile flash memory is provided so that data is not lost upon loss of power. The non-volatile flash memory stores both raw data and the appropriate measurement data under the control of a flash controller that enables the storage of such data with optimum power usage.

While the invention has been described in connection with a preferred embodiment, it is not intended to limit the scope of the invention to the particular form set forth, but, on the contrary, it is intended to cover such alternatives, modifications, and equivalents as may be included within the spirit and scope of the invention as defined by the appended claims.

We claim:

1. A battery operated ambulatory monitor for recording patient physiological data comprising:

a plurality of sensors for attachment to an ambulatory patient for providing analog signals to a plurality of input channels, said analog signals representing different physiological parameters including ECG, EEG, EMG, EOG, respiratory activities, respiratory mechanics, and blood oxygen saturation;

A-D converter means for converting said analog sensor signals to digital data;

processor means coupled to said A-D converter means for taking appropriate measurements from said digital data related to said physiological parameters;

digital storage means coupled to said processor means for storing both said physiological digital data and said appropriate measurements, said storage means comprising a non-volatile flash memory;

controller means coupled between said processor means and said flash memory for causing said digital data measurements and said physiological digital data to be transferred between said processor means and said flash memory in data blocks;

said controller means causing said processor means to be powered down between data block transfers to conserve power; and variable selection means in said processor means for selecting one or more of said channels providing said physiological parameters received from said sensors for processing and recording.

2. A monitor as in claim 1 wherein said input channels have bandwidths in the range of about 0.05 to about 1000 Hz.

3. A monitor as in claim 1 further including sample frequency controlling means in said processor for selectively varying the A-D converter sampling rate between 50–2000 samples per second.

4. A monitor as in claim 1 wherein said processor provides compression of said digital data representing said physiological parameters.

5. A monitor as in claim 1 wherein said input channels range in number from 1-to-p24.

6. A monitor as in claim 1 further comprising said controller means causing said flash memory to power down between data block transfers to conserve power.

7. An ambulatory monitoring device for recording patient physiological data to be used for subsequent medical diagnosis, said device comprising:

a plurality of input channels for receiving raw analog data signals representing different ones of said patient physiological data including ECG, EEG, EMG, EOG, respiratory activities, respiratory mechanics, and blood oxygen saturation;

A-D converter means for converting the raw analog data signals in each channel to raw digital data by sampling said raw analog data on each separate one of said channels at an individually selectable rate;

processor means coupled to said A-D converter for taking appropriate measurements of said raw digital data for storage;

a non-volatile digital flash memory coupled to said processor for storing both said raw digital data and said appropriate measurement data;

a flash controller coupled between said processor means and said flash memory for transfer to storage of both said raw data and said appropriate measurement data in blocks;

said controller causing said processor means to be powered down between data block transfers to conserve power; and selection means in said processor means for selecting one or more channels of said physiological data for processing and recording.

8. A monitoring device as in claim 7, wherein said input channels have bandwidths in the range of about 0.05 to about 1000 Hz.

9. A monitoring device as in claim 7 further including sample frequency controlling means in said processor for selectively varying the A-D converter sampling rate between 50–2000 samples per second.

10. A monitoring device as in claim 7 wherein said processor means provides compression of said digital data representing said physiological parameters.

11. A monitoring device as in claim 7 wherein the input channels range in number from 1-to-24.

12. A method of recording patient physiological data with an ambulatory monitor comprising the steps of:

attaching a plurality of sensors to an ambulatory patient for providing analog signals to a plurality of input channels, said analog signals representing different physiological parameters including ECG, EEG, EMG, EOG, respiratory activities, respiratory mechanics, and blood oxygen saturation;

converting said analog sensor signals to digital data with A-D converter means;

coupling processor means to said A-D converter means for taking appropriate measurements from said digital data related to said physiological parameters;

coupling digital storage means to said processor means for storing both said physiological digital data and said appropriate measurements, said storage means comprising a non-volatile flash memory;

coupling controller means between said processor means and said flash memory for causing said digital data measurements and said physiological digital data to be transferred to said flash memory in data blocks;

causing said power means to be powered down between data block transfers to conserve power; and selecting one or more of said channels providing said physiological parameters received from said sensors for processing and recording.

13. A method as in claim 12 further including the step of providing said input channels with bandwidths in the range of about 0.05 to about 1000 Hz.

14. A method as in claim 12 further including the step of selectively varying the A-D converter sampling rate between 50–2000 samples per second with a sample frequency controlling means in said processor.

15. A method as in claim 12 further including the step of providing compression of said digital data representing said physiological parameters.

16. A method as in claim 12 further including the step of providing said input channels ranging in number from 1-to-24.

17. A method for recording patient physiological data with an ambulatory device to be used for subsequent medical diagnosis, said method comprising the steps of:

receiving raw analog data signals from a plurality of input channels representing different ones of said patient physiological data including ECG, EEG, EMG, EOG, respiratory activities, respiratory mechanics, and blood oxygen saturation;

converting the raw analog data signals in each channel to raw digital data with A-D converter means by sampling said raw analog data on each separate one of said channels at an individually selectable rate;

taking appropriate measurements of said raw digital data for storage with processor means coupled to said A-D converter;

coupling a non-volatile digital flash memory to said processor for storing both said raw digital data and said appropriate measurement data;

coupling a flash controller between said processor means and said flash memory for transfer to storage of both said raw data and said appropriate measurement data in said memory in blocks;

powering down said processor means between data block transfers to conserve power; and selecting one or more channels of said physiological data for processing and recording with means in said processor means.

* * * * *